United States Patent [19]
Anderson, Jr.

[11] 3,941,816
[45] Mar. 2, 1976

[54] STABILIZED OXICHROMIC COMPOUNDS
[75] Inventor: Albert Edward Anderson, Jr., Rochester, N.Y.
[73] Assignee: Eastman Kodak Company, Rochester, N.Y.
[22] Filed: Dec. 10, 1971
[21] Appl. No.: 206,925

[52] U.S. Cl. ............... 260/404.5; 96/3; 96/56.1; 96/66 R; 96/73; 96/77; 96/99; 260/346.2 R; 260/456 A; 260/463; 260/477; 260/479 R; 260/559 R
[51] Int. Cl.² ........................................ C07C 103/76
[58] Field of Search..... 260/479 R, 476, 469, 404.5

[56] References Cited
UNITED STATES PATENTS
3,701,783  10/1972  Barr et al. .................... 260/516

Primary Examiner—James A. Patten
Attorney, Agent, or Firm—G. E. Battist

[57] ABSTRACT

Stabilized oxichromic compounds are disclosed, along with processes for stabilizing oxichromic compounds. In one aspect, the stabilized compounds are O-acylated compounds which contain a reduced azomethine linkage. In another aspect, the stabilized compounds are O-acylated compounds which can undergo base catalyzed chromogenic oxidation to produce a yellow dye.

10 Claims, No Drawings

STABILIZED OXICHROMIC COMPOUNDS

This invention relates to novel organic compounds and to processes for making these compounds. In one aspect, this invention relates to stabilized oxichromic compounds which form yellow dyes. In another aspect, this invention relates to O-acylated oxichromic developers which are useful in photography, for example, in diffusion transfer systems where a yellow dye can be formed upon chromogenic oxidation to provide a new chromophore. In still another aspect, this invention relates to an O-stabilized, oxichromic, yellow-forming compound having a reduced axomethine linkage.

It is known in the art to use developing agents in silver halide photographic systems which have a hydrolyzable group attached to one of the active positions of the developing agent, for example, as disclosed in U.S. Pat. No. 2,992,105. It is also known in the art to use dye developers which have hydrolyzable groups attached thereto in photographic systems such as, for example, in U.S. Pat. Nos. 3,230,082, 3,230,083 and 3,230,084 issued Jan. 18, 1966. Moreover, it is known in the art to use leuco dyes as developers in silver halide systems as disclosed in U.S. Pat. Nos. 3,065,074 and 2,909,430. However, many of these prior-art systems had undesirable characteristics such as poor absorption characteristics of the available dyes for color systems, low development rates, low image discrimination, and the like. Therefore, improved developers, dyes, photographic systems and image transfer systems were desired.

One highly improved photographic system with respect to the prior art is disclosed in U.S. Ser. No. 206,836 entitled "Oxichromic Compounds" by Lestina and Bush, filed Dec. 10, 1971, now abandoned and refiled as U.S. Ser. No. 308,869 on Nov. 22, 1972, the disclosure of which is incorporated herein by reference. In certain embodiments, the oxichromic developers disclosed are compounds which contain a developing agent moiety linked to another moiety which can be oxidized to produce a new chromophore (i.e., a useful dye moiety) which is useful in color photographic systems.

We have now discovered a new class of stabilized oxichromic compounds which can be used in photographic systems and are especially useful in the photographic systems of Lestina and Bush to provide improved photographic properties, keeping properties, stability, etc. The stabilized oxichromic compounds of this invention generally have the formula:

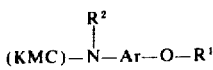

wherein (KMC) is an open-chain ketomethylene color coupler which couples at the carbon atom forming the methylene moiety (e.g.,

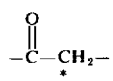

wherein * denotes the coupling position); the nitrogen atom of said formula is attached to (KMC) in the coupling position; Ar is an arylene group containing from 6 to about 20 carbon atoms including substituted arylene, unsubstituted arylene, fused-ring arylene and the like, and preferably is a phenylene group which preferably is substituted with halogen atoms or groups containing halogen atoms in the ortho or meta positions; $R^1$ is a carbonyl-containing group which forms an ester with the next adjacent atom shown in the formula, such as:

wherein $R^4$ is an alkyl group, an aryl group, a halogen-substituted alkyl or aryl group, an alkoxy group, a cycloalkyloxy group, an aryloxy group, a carbonyl-containing group and the like and is preferably an alkyl group containing from 1 to 6 carbon atoms or an aryl group containing from about 6 to 12 carbon atoms; and $R^2$ can be a hydrogen atom or the same substituents as $R^1$. While halogen-substituted stabilizing groups are sometimes preferred when acylating a nitrogen atom, we have found that alkyl or aryl groups are generally preferred when stabilizing a compound by acylation of an hydroxy group.

In another embodiment, this invention relates to oxichromic developers having the formula:

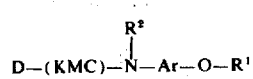

wherein D— is a group which is a silver halide developer including developers containing hydrolyzable groups thereon and is preferably a disubstituted aromatic group containing at least two substituents thereon which can be hydroxyl groups or hydrolyzable derivatives thereof, primary amino groups, or alkylamino groups including substituted alkylamino groups; (KMC) is an open-chain ketomethylene color coupler including, of course, linking groups connecting D, wherein the nitrogen atom in the formula is attached to (KMC) in a coupling position, and wherein (KMC) can contain the moiety:

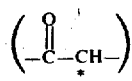

wherein * denotes the active methylene coupling position, and $R^1$, $R^2$ and Ar are as defined above.

Typically, Ar is the nucleus of an aminophenol compound such as those disclosed in Bush, Gates and Newmiller, U.S. Ser. No. 169,706 filed Aug. 6, 1971, now U.S. Pat. No. 3,791,827 which is incorporated herein by reference.

In a specific embodiment according to the invention, oxichromic compounds are prepared having the formula:

Cpd. 1 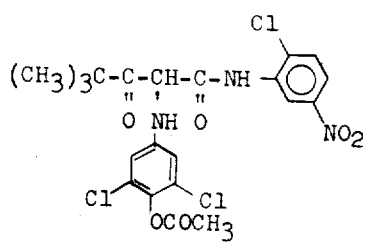
Cpd. 2 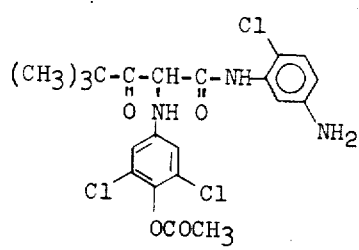
Cpd. 3 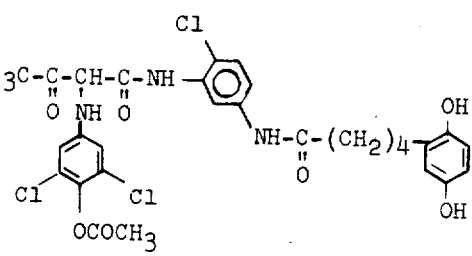
Cpd. 4 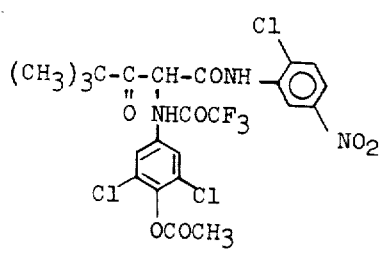
Cpd. 5 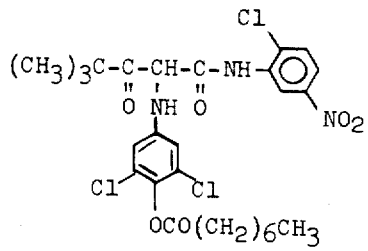
Cpd. 6 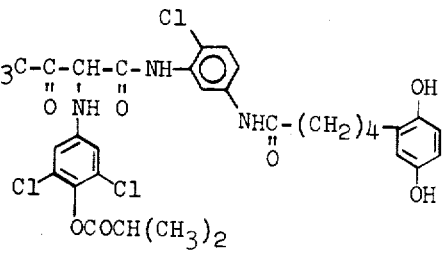
Cpd. 7 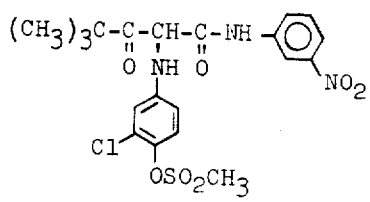

Cpd. 8

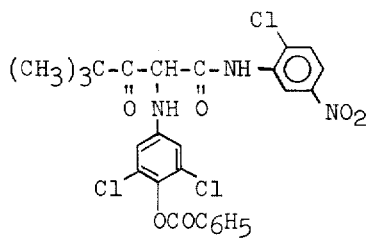

Cpd. 9

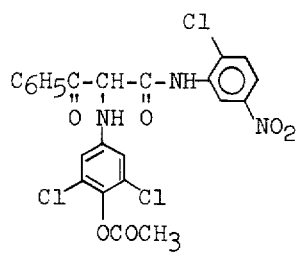

Cpd. 10

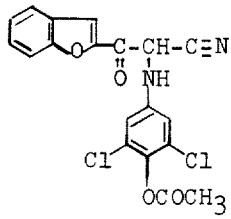

The term "oxichromic compound" as used herein is understood to refer to those compounds which undergo chromogenic oxidation wherein they can form a dye. The stabilized oxichromic compounds are those oxichromic compounds which contain a stabilizing group thereon to prevent premature oxidation and which stabilizing group can be readily removed, such as by contact with a strong alkaline solution to provide base catalyzed chromogenic oxidation.

The term "axomethine linkage" is understood to mean the grouping:

(>C=N—)

Preferably, the axomethine compounds of this invention are further defined as being indophenols, which is understood to refer to compounds having the general structure:

(COUP)=N—Ar—OH wherein (COUP) is a color coupler such as an open-chain ketomethylene coupler and Ar is as defined above.

Generally, the compounds of this invention are formed by reacting an open-chain ketomethylene compound, which is connected to a phenol group by a reduced azomethine linkage, with an equivalent amount of an appropriate acid halide in the presence of a base such as pyridine at temperatures between about −20° C. to about 20° C., and preferably between about 0°–5° C. The procedure appears to provide acylation exclusively on the hydroxyl group of the p-aminophenol, whereas acylation carried out with an acid anhydride or with other reaction conditions yields substantial N-acylation.

The reduced indophenols can be prepared as disclosed in the prior art by reacting oxidized aminophenols with color couplers and then reducing the chromophore azomethine group to form the leuco indophenol or, more preferably, the reduced indophenols can be made by reacting an α-halogenated open-chain ketomethylene color coupler with an unoxidized aminophenol as disclosed in Reardon, U.S. Ser. No. 206,927 entitled "Method of Preparing Indophenols and Oxichromic Compounds," filed on even date herewith and which is incorporated herein by reference; representative suitable open-chain ketomethylene color couplers are also disclosed in this incorporated application.

The inventive steps of this invention are further described with reference to the synthesis of an oxichromic developer.

Generally, the oxichromic developers of this invention can be prepared by (1) reacting an α-halogenated open-chain ketomethylene color coupler with an aminophenol to form a compound with a reduced azomethine linkage, (2) reacting the reduced azomethine compound with an acid chloride to provide O-acyl groups which stabilize the reduced azomethine linkage, (3) condensing the stabilized, reduced, azomethine compound with a masked silver halide developer, and (4) hydrogenolysis of the stabilized oxichromic developer to remove the masking groups from the silver halide developing group.

In step (1), the compound having the reduced azomethine linkage is provided by the processes as disclosed in Reardon, U.S. Ser. No. 206927 referred to above.

In step (2), the reduced azomethine compound is reacted with an acylating agent in a basic nonaqueous system with a polar solvent. The base serves as an acid acceptor and can be the same compound as the polar solvent such as, for example, pyridine. In another embodiment, the solvent is acetone and dimethylaniline is added as the acid acceptor. Typical useful acylating agents include N-acylimidazoles; acid halides such as cycloalkyloxyacetyl chlorides, aryloxyacetyl chlorides, methoxyacetyl chloride, ethoxyacetyl chloride, propoxyacetyl chloride, butoxyacetyl chloride, octyloxyacetyl chloride, isopropoxyacetyl chloride, isobutoxyacetyl chloride, p-nitrobenzoyl chloride, benzoyl chloride, anisoyl chloride, acetyl chloride, propionyl chloride, formyl fluoride, perfluorobutyl chloride, caproyl chloride, trichloroacetyl chloride, monochloroacetyl chloride, acrylyl chloride, succinoyl chloride, and the like; preferably, the acylating agent is an acid chloride. In those instances where the acylation procedure is carried out on a compound which contains a masked developer moiety, such as oxichromic developer, I have found that it is desirable to use weak bases such as tertiary amines to catalyse the esterification. Preferably, the acylatiion in this instance is carried out at a pH of less than 11 when stabilized oxichromic developers are prepared. However, in the preferred synthetic route as described in the immediate oxichromic developer preparation, a strong base can be used advantageously since the developer group is not introduced until later in the synthesis. The acylating agent is generally present in substantially equimolar ratio with the reduced azomethine compound; however, up to 10% excess can be used when achieving primarily O-acylation. The acylation reaction is preferably carried out at the temperatures indicated for time periods of up to 1 hour to achieve primarily O-acylation.

In step (3), the stabilized azomethine compound is reacted with a masked silver halide developer, preferably by a condensation reaction. The silver halide developing group is masked to prevent undesirable condensation reactions; preferably, the masking groups are groups which will hydrolyze at a pH of 12 or above, or more preferably are those which can be removed by hydrogenolysis, such as by catalytic reduction in an acid medium, or with a nucleophile other than an hydroxide such as, for example, thiourea to remove a chloroacetate blocking group. In one highly preferred embodiment of making the stabilized oxichromic developers of this invention, the masking group is a carbobenzoxy group and the like which will permit selective reactions to take place in the process, such as selective removal of the carbobenzoxy, etc. In step (4), the hydrogenolysis is preferably carried out with a strong reducing agent which is effective in removing the masking group from the active groups of the silver halide developing agent. Generally, the procedure is carried out by catalytic reduction in an acidic medium with a noble metal catalyst like palladium or with Raney nickel, using hydrogen as the reducing agent. Acetic acid in ethanol is useful to provide the acidic medium for this step and is especially useful when groups such as carbobenzoxy groups are to be removed. In another embodiment, the masking groups are removed with a nucleophile other than hydroxide such as, for example, thiourea when chloroacetate is used as a blocking group.

In some instances it is desirable to have a stabilizing group on the nitrogen atom of the azomethine group. This can be present before the O-stabilization reaction or can be attached after stabilizing groups have been put on either one or both of the oxygen atoms as described above; for example, a N-acyl group could be obtained by reacting one of the O-stabilized azomethine dyes of this invention with trifluoroacetic anhydride in tetrahydrofuran.

The use of a masked developing agent having groups such as carbobenzoxy groups is particularly advantageous in the process described above to prevent unwanted reactions and still provide a group which can be selectively removed. In the event that other hydrolyzable groups are desired on the developer portion of the stabilized oxichromic compounds of this invention, they can be substituted on the developer moiety after removal of the carbobenzoxy groups.

Generally, the stabilized oxichromic compounds of this invention can be used wherever it is desirable to generate a dye by a base catalyzed oxidation reaction. In one highly useful application, they can be used in photographic systems wherein colorless layers are desired for exposure, etc., and a dye is generated during development, such as in an imagewise manner. The compounds of this invention will remain colorless until they undergo a base catalyzed chromogenic oxidation wherein they will produce the chromophore of a dye.

In one specific useful application, the stabilized oxichromic developers of this invention are used in image transfer systems as described in Lestina and Bush, referred to above.

The invention can be further illustrated by the following examples of preferred embodiments thereof.

EXAMPLE 1:

Preparation of Compound 1

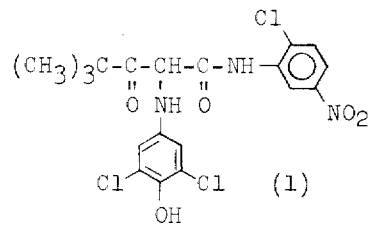

In 1 liter of dry pyridine, 142.5 g. (0.30 mole) of the leuco dye (1) are dissolved, cooled to 0° to 5° C., and stirred under nitrogen atmosphere while 23.5 ml. (0.33 mole) of acetyl chloride are added dropwise. After the addition is complete (about 15 minutes), the reaction is allowed to stir and warm slowly to room temperature (total time, 1 hour). A light yellow oil is obtained when the reaction mixture is added to an excess of water with stirring. The aqueous supernatant liquid is decanted from the oil. About 500 ml. methanol are added to the oil with stirring. The oil briefly dissolves in the methanol and then an almost colorless solid precipitates. This is collected by suction, washed with methanol and dried in air; weight, 136.4 g. (88% yield); m.p. 176.5°–178.5° C. Infrared evaluation shows a carbonyl peak at 1755 cm$^{-1}$ indicating that the acetyl group has been attached to the phenolic hydroxyl group and not the amine.

Calculated for $C_{21}H_{20}Cl_3N_3O_6 \cdot \frac{1}{2}C_6H_6$: C, 51.86; H, 4.17; Cl, 19.14; N, 7.56. Found: C, 51.4; H, 4.0; C, 51.8; H, 4.2; Cl, 19.1; N, 7.5.

The product is believed to have the formula of Compound 1 identified above.

EXAMPLE 2:

Preparation of Compound 5

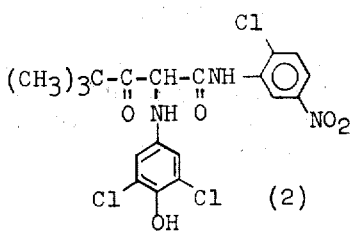

In 50 ml. dry pyridine under nitrogen, 4.74 g. (0.010 mole) of (2) are dissolved and cooled to 0° C. while 1.84 ml. (0.011 mole) of octanoyl chloride are added dropwise with stirring. After allowing the reaction to warm to room temperature (total time, 1 hour), the reaction mixture is poured with stirring into an excess of water. The light yellow oil which separates gradually solidifies with stirring; wt. light yellow solid, 6.00 g. (100% yield); m.p. 120°–125° C. After one recrystallization from cyclohexane, 4.60 g. of a light yellow crystalline solid are obtained, m.p. 126°–127° C. The IR curve shows an ester carbonyl peak at 1775 cm$^{-1}$ and mass spec conforms the structure; m.p. 127.5°–129° C. Calculated for $C_{27}H_{32}Cl_3N_3O_6$: C, 54.0; N, 5.50; Cl, 17.7. Found: C, 54.1; N, 5.6; Cl, 17.8.

This compound is believed to have the formula of Compound 5 identified above.

EXAMPLE 3:

A. Preparation of Intermediate 3-A

In 750 ml. tetrahydrofuran, 136.4 g. (0.264 mole) of Compound 1 are dissolved, Raney Nickel catalyst added and hydrogenated for 1 hour at 40° C. until hydrogenation is complete. The reaction mixture is cooled and catalyst is filtered from the reaction mixture, which in turn is added to an excess of water, with stirring. A colorless oil separates, which gradually solidifies with continued stirring and adding seed crystals of a previously prepared sample. The colorless solid is filtered from the solution, washed with water and dried; weight, 118.8 g. (92.3% yield). The IR curve shows an ester >C=O peak at 1765 cm$^{-1}$. Calculated for $C_{21}H_{22}Cl_3N_3O_4$: C, 51.82; N, 4.56; N, 8.63. Found: C, 52.6; N, 4.5; N, 8.9; 52.6; C, 52.06; N, The structure is believed to have the formula:

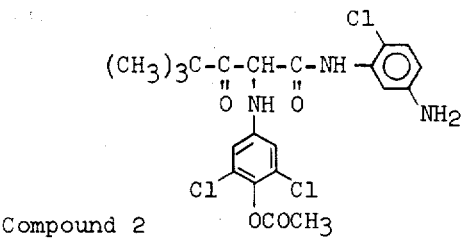

Compound 2

B. Preparation of Intermediate 3-B

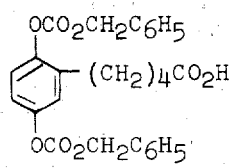

Acid A

In 25 ml. SOCl$_2$ containing a trace amount of dimethylformamide, 27.0 g. (0.0564 mole) of Acid A are dissolved and refluxed on the steam bath for 5 minutes. The thionyl chloride is then removed in vacuo. The semi-solid obtained is triturated twice with ligroin which in turn is removed in vacuo. The oil is then dissolved in carbon tetrachloride and passed over ice in a funnel. The carbon tetrachloride solution is dried over anhydrous sodium sulfate and then solvent removed in vacuo. The light yellow oil is dissolved in 50 ml. of dry acetone.

C. Preparation of Intermediate 3-C

In 200 ml. of dry acetone under nitrogen at room temperature, 25.0 g. (0.0513 mole) of Intermediate 3-A are dissolved and stirred while the acetone solution of Intermediate 3-B is added dropwise. After 1 hour, the acetone solution is added to an excess of water with stirring. The oil which separates is extracted with benzene, washed with an aqueous sodium bicarbonate solution, followed by water. The dried benzene solution is evaporated to dryness in vacuo to give a light yellow glass. This is purified by dissolving in ethyl acetate and reprecipitating by adding an excess of n-hexane; 43.3 g. (81% yield) of an amorphous, almost colorless solid (Compound 3-C) are obtained.

D. Preparation of stabilized oxichromic developer

In 250 ml. absolute ethanol containing 2.5 ml. glacial acetic acid, 20.0 g. (0.0211 mole) of Compound 3-C are dissolved, palladium charcoal catalyst added and hydrogenated for 1 hour at 40° C. and 40 psi. TLC (thin-layer chromatography) indicates that the reaction is incomplete, so additional catalyst is added and hydrogenation is continued for 1½ hours longer. The hydrogenation is then stopped, catalyst filtered and solvent removed in vacuo. The glass obtained is dissolved in hot benzene, filtered, and added to an excess of n-hexane with stirring; 12.2 g. (85% yield) of a white amorphous solid are obtained; m.p. 78°–80° C. (softening). The IR curve shows an ester carbonyl peak at 1760 cm$^{-1}$. Calculated for $C_{32}H_{34}Cl_3N_3O_7$: C, 56.61; N, 5.05; Cl, 15.66 Found: C, 56.1; N, 5.6; Cl, 15.3; Cl, 15.4

The compound is believed to have the formula:

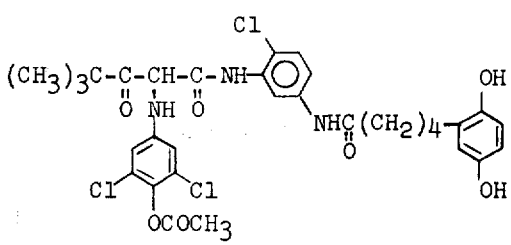

EXAMPLE 4:

This example demonstrates the imagewise transfer of the oxichromic developer of Example 3 from an exposed silver halide element to a receiver sheet during processing. Also demonstrated is the chromogenic oxidation to the desired hue which accompanies processing.

A. A light-sensitive element is coated with the following layers on a transparent support;
1. layer containing 125 mg./ft.² of gelatin, 75 mg./ft.² of diethyl lauramide and 40 mg./ft.² of the stabilized oxichromic developer of Example 3;
2. silver halide layer containing 100 mg./ft.² of gelatin, 100 mg./ft.² of silver and 10 mg./ft.² of 1-phenyl-3-pyrazolidone
3. layer containing 80 mg./ft.² of gelatin.

B. A sample of the element A above is exposed through a graduated-density test object. The sample is thereafter spread with a 0.004 inch layer processing fluid of composition shown in C below.

C. Processing fluid:

| KOH | 40 g./l. |
| hydroxyethyl cellulose | 30 g./l. |
| pH 13.7 | |

Immediately following application of this fluid, the coated surface is laminated to a mordanted receiver containing the mordant N-n-octadecyltributylammonium bromide in a gelatin layer.

After 1 minute of contact, the mordanted layer is peeled off showing a well-defined yellow-colored positive reproduction of the test object.

EXAMPLE 5:

An oxichromic developer is prepared by the procedure of Example 3 using Compound 5 of Example 2 as the starting stabilized oxichromic compound. The product is believed to have the formula:

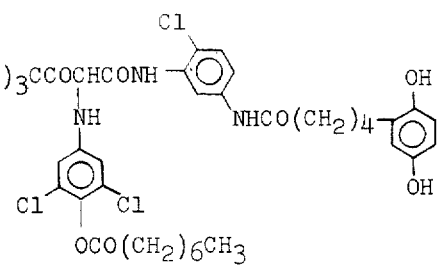

Compound 11        m.p. 90° C.

EXAMPLE 6:

Additional oxichromic compounds are prepared according to Examples 1 and 2 and further reacted in accordance with Example 3 to produce the following oxichromic developers:

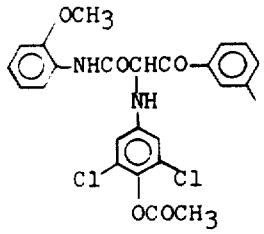

Compound 12        m.p. 120-130° C. dec.

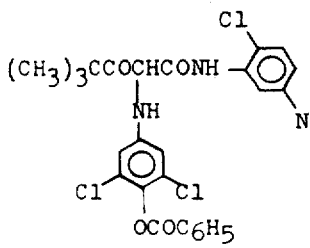

Compound 13        m.p. 120° C.

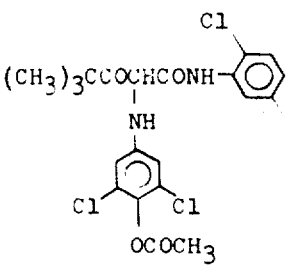

Compound 14        m.p. 70-75° C.

Compound 15

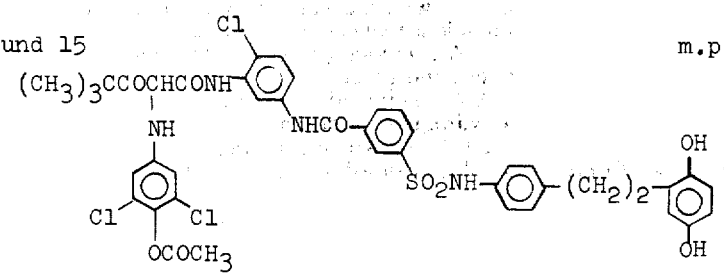

m.p. 125° C.

Compound 16

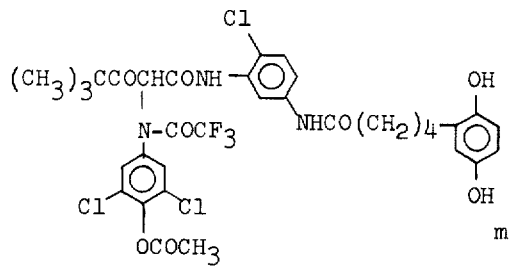

m.p. 167–171° C.

These oxichromic developers are then incorporated in photographic elements according to Example 4 with similar results.

Although the invention has been described in considerable detail with particular reference to certain preferred embodiments thereof, variations and modifications can be effected within the spirit and scope of the invention.

I claim:

1. A compound having the formula:

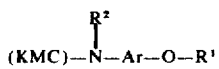

wherein $R^1$ is a group of the formula:

wherein $R^4$ is an alkyl group containing from 1–6 carbon atoms or an aryl group containing from 6–12 carbon atoms; Ar is an arylene group having from about 6–20 carbon atoms; $R^2$ can be a hydrogen atom or the same substituents as $R^1$; and (KMC) is an open-chain ketomethylene color coupler containing a group of the formula:

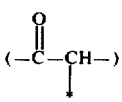

wherein * represents the coupling position which forms a bond with the said nitrogen atom attached to Ar to provide a reduced azomethine linkage.

2. A compound according to claim 1 wherein $R^1$ is an acetyl group.

3. A compound according to claim 1 wherein Ar is a phenylene group.

4. A compound according to claim 1 wherein $R^4$ is an alkyl group containing from 1–4 carbon atoms.

5. A compound having the formula:

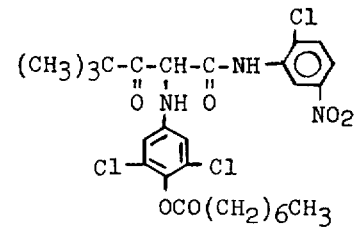

6. A compound having the formula:

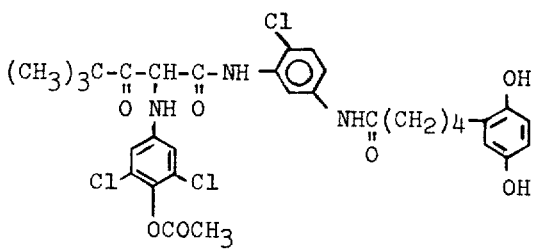

7. A compound of the formula:

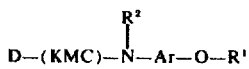

wherein D— is an aromatic nucleus which is disubstituted with hydroxyl groups, primary amino groups or alkylamino groups to provide a silver halide developer; $R^1$ is a group of the formula:

wherein $R^4$ is an alkyl group containing from 1–6 carbon atoms or an aryl group containing from 6–12 carbon atoms; Ar is an arylene group having from about 6–20 carbon atoms; $R^2$ can be a hydrogen atom or the same substituents as $R^1$; and (KMC) is an open-chain ketomethylene color coupler containing a group of the formula:

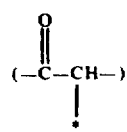
wherein * represents the coupling position which forms a bond with the said nitrogen atom attached to Ar to provide a reduced azomethine linkage.
8. A compound according to claim 7 wherein Ar is a phenylene group.
9. A compound according to claim 7 wherein D— is a hydroquinone group.
10. A compound according to claim 7 wherein Ar is a halogen-substituted arylene group.
* * * * *

UNITED STATES PATENT AND TRADEMARK OFFICE
CERTIFICATE OF CORRECTION

PATENT NO. : 3,941,816
DATED : March 2, 1976
INVENTOR(S) : Albert Edward Anderson, Jr.

It is certified that error appears in the above-identified patent and that said Letters Patent are hereby corrected as shown below:

Column 1, line 14, "axomethine" should read --azomethine--. Column 2, line 64, after "3,791,827", --,-- should be inserted. Column 5, line 42, "axomethine" should read --azomethine--; line 48, "axomethine" should read --azomethine--. Column 7, line 21, "catalyse" should read --catalyze--; line 22, "acylatiion" should read --acylation--. Column 9, line 57, "52.6" (2nd occurrence) should be placed directly under "52.6" (1st occurrence); the remainder of the line, "C, 52.06; N,", should be deleted; and --4.8;-- should be inserted directly under "8.9". Column 14, lines 53-54, "disubstitued" should read --disubstituted--.

Signed and Sealed this

*eighth* Day of *June 1976*

[SEAL]

Attest:

RUTH C. MASON
*Attesting Officer*

C. MARSHALL DANN
*Commissioner of Patents and Trademarks*